United States Patent
Lequette et al.

(10) Patent No.: US 11,819,287 B2
(45) Date of Patent: Nov. 21, 2023

(54) UNIVERSAL NAVIGATION INSTRUMENT ADAPTER

(71) Applicant: Zimmer Biomet Spine, Inc., Westminster, CO (US)

(72) Inventors: Samuel Lequette, Pessac (FR); Nicolas Bidegaimberry, Gradignan (FR); Nicolas Roche, Saint Medard en Jalles (FR); David Rigotto, Saint Selve (FR)

(73) Assignee: Zimmer Biomet Spine, Inc., Westminster, CO (US)

( * ) Notice: Subject to any disclaimer, the term of this patent is extended or adjusted under 35 U.S.C. 154(b) by 763 days.

(21) Appl. No.: 16/710,622

(22) Filed: Dec. 11, 2019

(65) Prior Publication Data
US 2020/0188034 A1 Jun. 18, 2020

Related U.S. Application Data (60) Provisional application No. 62/780,800, filed on Dec. 17, 2018.

(51) Int. Cl.
*A61B 34/20* (2016.01)
*A61B 34/00* (2016.01)
(Continued)

(52) U.S. Cl.
CPC .............. *A61B 34/20* (2016.02); *A61B 34/25* (2016.02); *A61B 90/57* (2016.02);
(Continued)

(58) Field of Classification Search
CPC . A61B 34/20; A61B 2034/2046; A61B 34/25; A61B 90/57; A61B 2090/3983; A61B 2017/00477; A61B 2562/16
See application file for complete search history.

(56) References Cited

U.S. PATENT DOCUMENTS 5,987,960 A 11/1999 Messner et al.
6,190,395 B1 * 2/2001 Williams ............... A61B 34/20
606/130

(Continued)

FOREIGN PATENT DOCUMENTS

| EP | 1570791 | 9/2005 |
|---|---|---|
| EP | 2830528 | 2/2015 |
| WO | WO 99/26549 | 6/1999 |

OTHER PUBLICATIONS

Maxtorque datasheet; published in 2016 (Year: 2016).*
Search Report for European Patent Application No. 19217196.5, dated May 12, 2020 7 pages.

*Primary Examiner* — Chao Sheng
(74) *Attorney, Agent, or Firm* — Sheridan Ross P.C.

(57) ABSTRACT

A device or system to adapt navigation trackers from various manufacturers to a variety of instruments to be navigated during a surgical procedure is disclosed. An adapter for coupling a navigation tracking array to an instrument including a drive shaft and a tracking device holder. The drive shaft can include a handle interface, an instrument connection, and an intermediate section including a circular locking groove extends proximally from a positioning flange. The tracking device holder can be configured to secure a navigation tracking array to the drive shaft and include an elongated body and a locking button. The elongated body can include an inner bore extending along a longitudinal length of the elongated body and adapted to receive the intermediate section of the drive shaft. The locking button can retain the tracking device holder along the drive shaft while allowing for rotation about the longitudinal axis.

22 Claims, 5 Drawing Sheets

(51) Int. Cl.
*A61B 90/57* (2016.01)
*A61B 17/00* (2006.01)
*A61B 90/00* (2016.01)

(52) U.S. Cl.
CPC ............ *A61B 2017/00477* (2013.01); *A61B 2034/2046* (2016.02); *A61B 2090/3983* (2016.02); *A61B 2562/16* (2013.01)

(56) References Cited

U.S. PATENT DOCUMENTS

| | | | |
|---|---|---|---|
| 6,556,857 B1 | 4/2003 | Estes et al. | |
| 6,772,002 B2 | 8/2004 | Schmidt et al. | |
| 6,796,988 B2 | 9/2004 | Melkent et al. | |
| 6,947,783 B2 | 9/2005 | Immerz | |
| 7,166,114 B2 | 1/2007 | Moctezuma De La Barrera et al. | |
| 7,217,276 B2 | 5/2007 | Henderson et al. | |
| 7,477,926 B2 | 1/2009 | Mccombs | |
| 7,668,584 B2 | 2/2010 | Jansen | |
| 7,688,998 B2 | 3/2010 | Tuma et al. | |
| 7,771,436 B2 | 8/2010 | Moctezuma De La Barrera et al. | |
| 7,862,568 B2 | 1/2011 | Vilsmeier et al. | |
| 7,873,400 B2 | 1/2011 | Moctezuma De La Barrera et al. | |
| 7,877,890 B2 | 2/2011 | Weber | |
| RE42,194 E | 3/2011 | Foley et al. | |
| 7,993,353 B2 | 8/2011 | Roßner et al. | |
| 8,105,339 B2 | 1/2012 | Melkent et al. | |
| RE43,328 E | 4/2012 | Foley et al. | |
| 8,961,500 B2 | 2/2015 | Dicorleto et al. | |
| RE45,484 E | 4/2015 | Foley et al. | |
| 9,050,108 B2 | 6/2015 | Grinberg et al. | |
| 9,271,804 B2 | 3/2016 | Wu | |
| 9,393,039 B2 | 7/2016 | Lechner et al. | |
| 9,451,999 B2 | 9/2016 | Simpson et al. | |
| 9,456,827 B2 | 10/2016 | Grinberg et al. | |
| 9,468,427 B2 | 10/2016 | Dicorleto et al. | |
| 9,877,786 B2 | 1/2018 | Zastrozna | |
| 2001/0037114 A1* | 11/2001 | Dinger | A61B 17/1688 606/171 |
| 2009/0042416 A1* | 2/2009 | Sigg | H05K 3/326 439/78 |
| 2015/0105833 A1* | 4/2015 | Simpson | A61B 17/8875 606/86 R |
| 2018/0028266 A1* | 2/2018 | Barnes | A61B 34/20 |
| 2018/0344304 A1* | 12/2018 | Lindenmann | B23B 31/223 |

* cited by examiner

UNIVERSAL NAVIGATION INSTRUMENT ADAPTER

CLAIM OF PRIORITY

This application claims the benefit of U.S. Provisional Patent Application Ser. No. 62/780,800, filed on Dec. 17, 2018, the benefit of priority of which is claimed hereby, and which is incorporated by reference herein in its entirety.

TECHNICAL FIELD

This document pertains generally, but not by way of limitation, to devices and methods for optical navigation assisted surgical procedures, such as those involving navigation of instruments for implanting pedicle screws in vertebral bodies, among others. More specifically, but not by way of limitation, the present application relates to a universal adapter for use in adapting various types of navigation tracking arrays to a variety of surgical instruments.

BACKGROUND

Imaging of anatomical features can be useful in preparing for and performing surgical procedures. In some procedures it can be desirable to register the shape of the anatomy in the obtained images with another frame of reference, such as the physical space of an operating room. The physical space of the operating room can be correlated to a frame of reference for using a surgical navigation system to assist in orienting instruments in reference to pre-operative imaging. Navigation of instruments used for inserting implants can assist surgeons in proper placement and orientation to avoid delicate tissues such as nerves or blood vessels. While it is relatively common for surgical centers to have an optical navigation system, there are many different providers of optical navigation systems that often utilize different navigation tracking arrays. Conversely, implant manufactures typically supply customized instruments designed specifically for manipulating their implants. Accordingly, the implant manufactures are often left to determine how best to enable a surgeon to navigate the implant specific instruments.

Overview

The present inventors have recognized, among other things, that a problem to be solved can include the difficulty or inability to track instruments not specifically designed to receive a navigation tracking array from a particular manufacturer. For example, if a surgical center only maintains a navigation system from manufacturer X, but the surgeon wants to navigate instruments supplied by manufacturer Y—those instruments will only be usable with the available navigation system if the instruments can receive the necessary tracking array. Adding to the challenge is the fact that the navigation tracking arrays must be affixed securely and repeatably to the surgical instruments in order to ensure accurate navigation, while avoiding constant recalibration of the instrument.

The present subject matter can provide a solution to these and other problems, such as by providing a universal adapter that is capable of coupling navigation tracking arrays from a wide variety of navigation system providers to instruments from various implant manufacturers. In an example, a universal adapter can include a drive shaft for coupling to an instrument and a tracking device holder to secure a navigation tracking array. In this example, the drive shaft can include a proximal handle interface, a distal instrument connection, and an intermediate section extending proximally from a distal positioning flange. The intermediate section can include an enlarged diameter and a circular locking groove. The tracking device holder can include an elongated body and a locking button. In this example, the elongated body can include an inner bore extending along a longitudinal length of the elongated body and adapted to receive the intermediate section of the drive shaft. The locking button can be engagable with the circular locking groove to retain the tracking device holder in a fixed axial position along a longitudinal axis of the drive shaft, while allowing for rotation of the tracking device holder about the longitudinal axis.

Another example can include a universal adapter apparatus comprising a drive shaft and a tracking device holder. The drive shaft can include a proximal handle interface, a distal instrument connection, and an intermediate section extending proximally from a distal positioning flange. The intermediate section can include a circular locking groove, a distal instrument connection adapted to removably and securely couple a proximal end of a plurality of instruments to the drive shaft. The tracking device holder can be adapted to maintain a navigation tracking array in a fixed axial position relative to a longitudinal axis of the drive shaft. In this example, the tracking device holder can include an elongated body and a tracking array pedestal. The elongated body can include an inner bore extending along a longitudinal length of the elongated body and can be adapted to engage a portion of the intermediate section of the drive shaft and abut the distal positioning flange, while remaining rotatable around the longitudinal axis of the drive shaft. The tracking array pedestal is coupled to the elongated body via an extension rod and includes a plurality of locating pins, where the universal support adapted to couple navigation tracking arrays with a plurality of clamping mechanisms to the tracking device holder.

This overview is intended to provide an overview of subject matter of the present patent application. It is not intended to provide an exclusive or exhaustive explanation of the invention. The detailed description is included to provide further information about the present patent application.

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

As discussed above, the present subject matter involves designs for a universal adapter to attach various navigation tracking arrays to a variety of instruments. The universal adapters disclosed include an instrument connection that securely and repeatably couples a surgical instrument to the universal adapter. The instrument connection can include an instrument nut that is tightened to secure the instrument within a drive socket at the end of an instrument bore on a distal end of a drive shaft that runs through the universal adapter. The opposite end of the drive shaft can include an interface to allow attachment of a handle or in certain examples a powered driver.

The body of the universal adapter can be rotatably coupled to an intermediate portion of the drive shaft, which includes a positioning flange to maintain a repeatable axial position along an instrument axis. The body also can include a tracking array pedestal extending radially away from a longitudinal axis of the drive shaft (which is aligned with the instrument axis once an instrument is attached). The tracking array pedestal can receive a proprietary navigation tracking array directly or it can receive a universal support with clamping positions for various different navigation tracking arrays from major navigation system suppliers. For example, a version of the universal support discussed below can receive navigation tracking arrays from suppliers such as Medtronic (SureTrackII) or BrainLab, among others.

In an example, the universal adapter is used on instruments for spinal fusion surgeries. Instruments that can be coupled to the universal adapter can include taps, probes, and screwdrivers, among others. The instrument connection can include a drive socket that accepts instruments with the following connection standards, ¼" (¼ inch or quarter-inch), AO large, and AO standard connections.

Figures 1A, 1B, 1C:
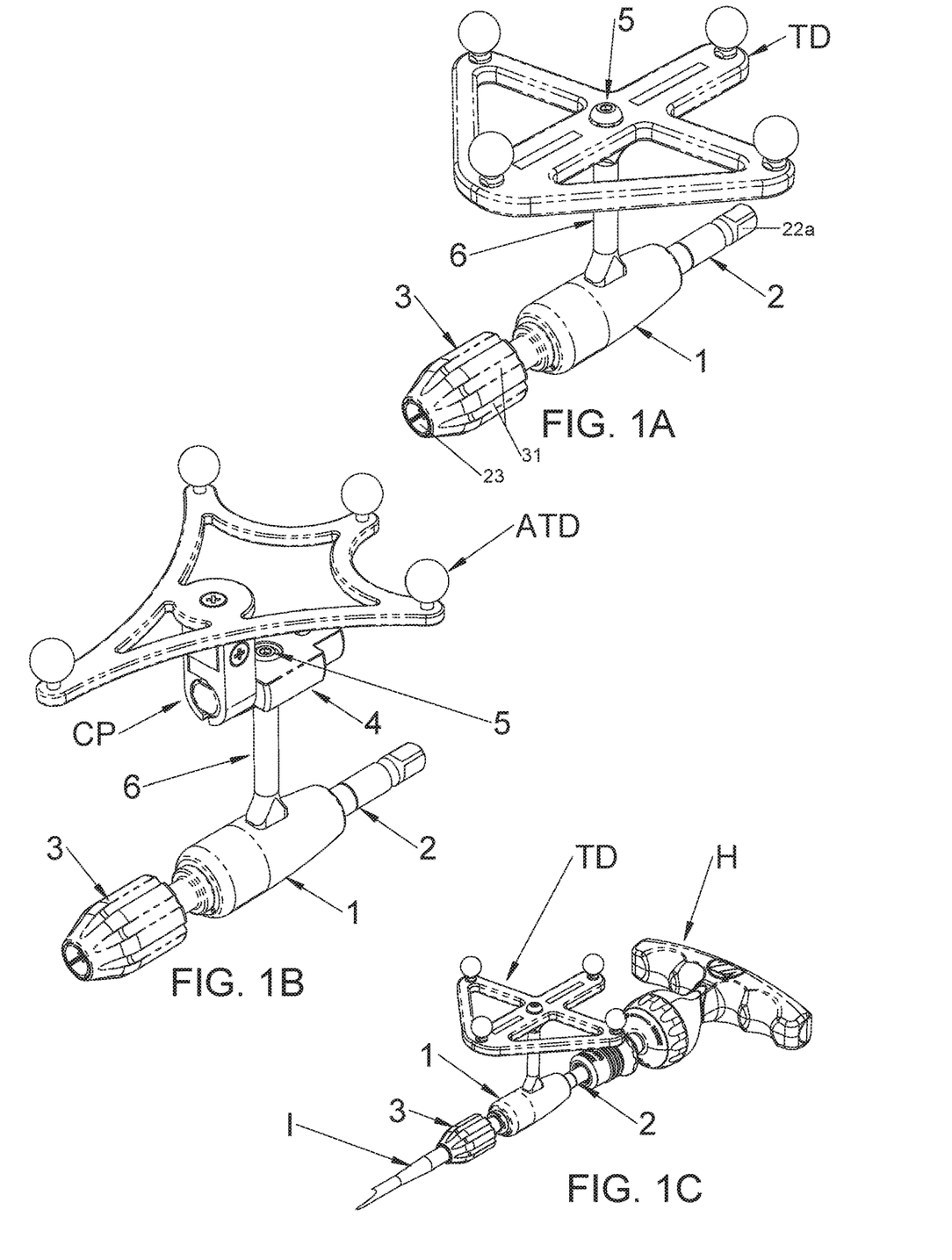
FIG. 1A is a perspective view of a universal instrument adapter securing a first style of navigation tracking array, in accordance with an exemplary embodiment.
FIG. 1B is a perspective view of a universal instrument adapter securing an alternative style of navigation tracking array, in accordance with an exemplary embodiment.
FIG. 1C is a perspective view of a universal instrument adapter securing a first style of navigation tracking array and including an instrument and handle, in accordance with an exemplary embodiment.

FIG. 1A is a perspective view of a universal instrument adapter securing a first style of navigation tracking array (TD), in accordance with an exemplary embodiment. In this example, the universal instrument adapter can include a tracking device holder (1), a drive shaft (2), an instrument nut (3), a tracking array pedestal (6), and a square drive handle connection (22a). In this example, the instrument nut (3) is part of the instrument connection (23). The instrument nut (3) can include grooves (31) distributed radially around the outer circumference. The grooves (31) assist with grip in tightening the instrument nut (3) to secure the instrument connection (23). In this example, the universal adapter is configured to receive a proprietary navigation tracking array (TD), which is secured directly to the tracking array pedestal (6) via a screw (5). The proprietary navigation tracking array (TD) is a tracking array designed specifically to interface with the universal adapter without use of a clamp or other intermediate connection.

FIG. 1B is a perspective view of a universal instrument adapter supporting an alternative style of navigation tracking array, in accordance with an exemplary embodiment. In this example, the universal instrument adapter is configured to receive an alternative tracking array (ATD) via a clamp (CP). The universal instrument adapter can include a tracking device holder (1), a drive shaft (2), an instrument nut (3), and a universal support (4) affixed to the tracking array pedestal (6) via screw (5). As in other examples, the drive shaft (2) can extend through the tracking device holder (1), which is able to rotate about a longitudinal (or instrument) axis running the length of the universal adapter. In this example, the universal support (4) includes at least three different interface positions, with the example alternative tracking array (ATD) clamped to the distal most interface in this example. In other examples, the universal support (4) can include more or fewer interface positions.

FIG. 1C is a perspective view of a universal instrument adapter supporting a first style of navigation tracking array (TD) and including an instrument (I) and handle (H), in accordance with an exemplary embodiment. In this example, the universal adapter is illustrated coupled to a proximal end of an instrument (I) and with a handle (H) connected to the square drive (22a) interface on the proximal end of the drive shaft (2). During use, the universal adapter is designed to be held in one hand by the tracking device holder (1) with the other hand able to manipulate the instrument (1) via the handle (H). In this example, the instrument nut (3) portion of the instrument connection is illustrated securing the instrument to a distal end of the drive shaft (2). Attaching the instrument (I) is done by inserting the proximal end of the instrument into the instrument connection (23) on the distal end of the drive shaft (2) and tightening the instrument nut (3), which reduces the diameter of an instrument bore receiving the instrument (I) within the instrument connection (23). The reduction of the diameter of the instrument bore results in the instrument (I) being securing retained within a drive socket within the instrument connection (23).

Figure 2A:
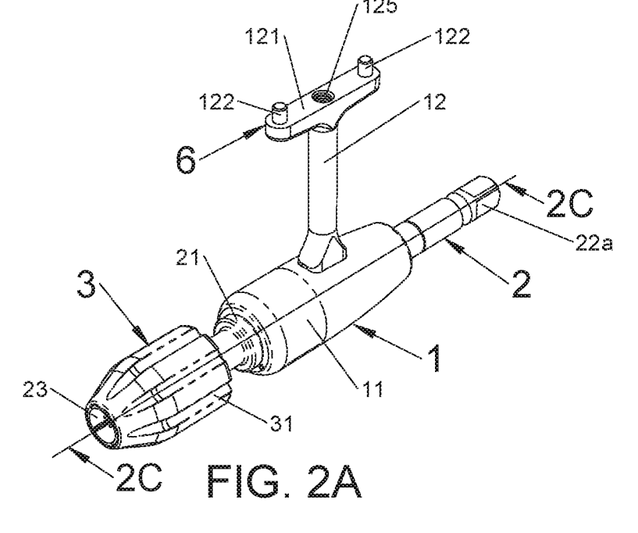
FIG. 2A is a perspective view of a universal instrument adapter without a navigation tracking array attached, in accordance with an exemplary embodiment.

FIG. 2A is a perspective view of a universal instrument adapter without a navigation tracking array attached, in accordance with an exemplary embodiment. In this example, additional features of the universal adapter are evident, such as the positioning flange (21), the extension rod (12), interface surface (121), positioning pins (122), and threaded hole (125). In this example, the positioning flange (21) is shown directly distal of, and abutting, the adapter body (11) of the tracking device holder (1). As discussed in additional detail below, the adapter body (11) includes a distal surface that abuts a proximal surface on the positioning flange (21), which is designed to maintain a constant axial position along the longitudinal axis of the tracking device holder (1). In other words, the positioning flange (21) operates to maintain a relative axial position between an instrument (I) and a tracking array, such as the first style tracking array (TD).

Figure 2B:
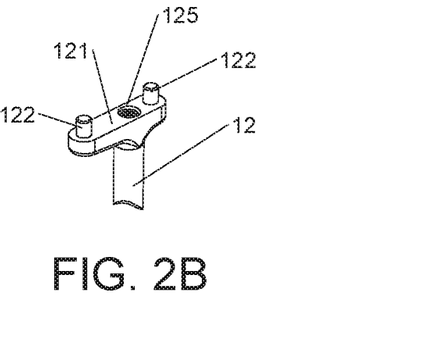
FIG. 2B is a detail view of a portion of a tracking array pedestal, in accordance with an exemplary embodiment.

FIG. 2B is a detail view of a portion of a tracking array pedestal (6), in accordance with an exemplary embodiment. In this example, the superior portion of the tracking array pedestal (6) is illustrated as including a superior end of the extension rod (12), an interface surface (121), a pair of positioning pins (122), and a threaded hole (125). The example shown in FIG. 2B differs from the example shown in FIG. 2A, in that the positioning pins (122) are not evenly offset from the threaded hole (125) in this example. The uneven offset in this example can provide a mechanism to ensure proper distal-proximal alignment of a tracking array upon engagement with the tracking array pedestal (6). With the positioning pins (122) unevenly offset from the threaded hole (125), a tracking array will only be able to be secured in a single orientation relative to the universal adapter. In other examples, the positioning pins (122) can include distinct pin shapes to further confine potential orientations of attachment for a tracking array. The positioning pins (122) can also be tapered to assist in aligning a tracking array, while ensuring a precise final position with reference to the tracking device holder (1) once the tracking array is secured.

Figure 2C:
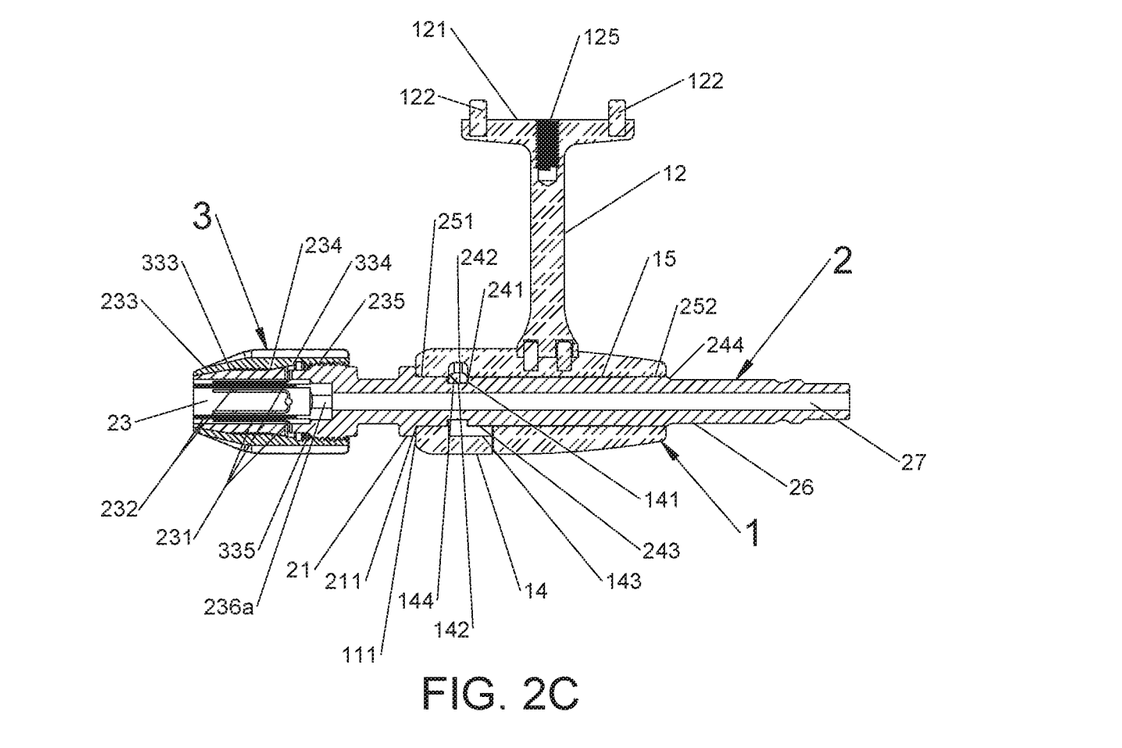
FIG. 2C is a cut-away view of a universal instrument adapter, in accordance with an exemplary embodiment.

FIG. 2C is a cut-away view of a universal instrument adapter, in accordance with an exemplary embodiment. In this example, additional details of the instrument connection (23) tracking device holder (1), and locking button (14) are illustrated. The cut-away view of the tracking device holder (1) depicts the adapter stop face (111) abutted with the positioning flange face (211). In this example, both the adapter stop face (111) and the positioning flange face (211) are perpendicular to the longitudinal axis of the universal adapter. In this example, the longitudinal axis can be understood with respect to the cannulation bore (27) running the length of the universal adapter along the longitudinal axis. The tracking device holder (1) is also shown as including a device holder inner bore (15), which receives intermediate cylinders (251, 252) of the drive shaft (2) to radially position the tracking array holder (1). The drive shaft (2) includes a proximal shaft bevel (244) to ease transition between the intermediate shaft diameter (26) and intermediate cylinders (251, 252), which include a larger diameter than the intermediate shaft diameter (26). The intermediate cylinders (251, 252) can be separated by a circular locking groove (242), where the circular locking groove (242) is a section of reduced diameter between distal intermediate cylinder (251) and proximal intermediate cylinder (252). The area of the drive shaft (1) interacting with the locking button (14) can include a shaft lock section (243). The shaft lock section (243) can include a reduced diameter section, in comparison to the distal intermediate cylinder (251) and the proximal intermediate cylinder (252). In an example, the shaft lock section (243) can provide for clearance from the internal diameter of the adapter to reduce friction. In this example, the circular locking groove (242) includes a further reduced diameter section within or adjacent to the shaft lock section (243).

In this example, the instrument connection (23) is fom1ed on a distal end of the drive shaft (2), which includes a ¼" (¼ inch or quarter-inch) square drive socket (236a) proximal of a collapsing bore area including slot openings (231, 232) and instrument connection conical interfaces (233, 234). In other examples, different types of drive socket can be included within the instrument connection (23). In this example, the instrument connection (23) also includes shaft threads 235, which are engaged by nut threads 335. The instrument nut (3) also can include distal conical interfaces (333, 334) that engage the instrument connection conical interfaces (233, 234) to effectively reduce the bore diameter and secure an instrument within the instrument connection (23). In some examples, the bore portion of the instrument connection (23) can be an enlarged extension of the cannulation bore (27) running through the remainder of the universal adapter. The bore of the instrument connection (23) can be enlarged in comparison to the other portions of the cannulation bore (27), and the cannulation bore (27) can be sized and positioned to align with a cannulation bore within an instrument secured within the instrument connection (23).

In this example, as the nut threads (335) of the instrument nut (3) are threaded onto the shaft threads (235) and the distal conical interfaces (333, 334) engage the instrument connection conical interfaces (233, 234) to reduce (e.g. controllably collapse) the diameter of the bore of the instrument connection (23). The reduction in the diameter of the instrument connection (23) results in securing an instrument seated in a drive socket, such as the ¼" (¼ inch or quarter-inch) square female drive socket (236a). The slot openings (231, 232), discussed in additional detail below, assist in allowing the instrument connection (23) to secure an instrument through threading the instrument nut (3) onto the drive shaft (2).

Figures 3A, 3B, 3C, 3D, 3E:
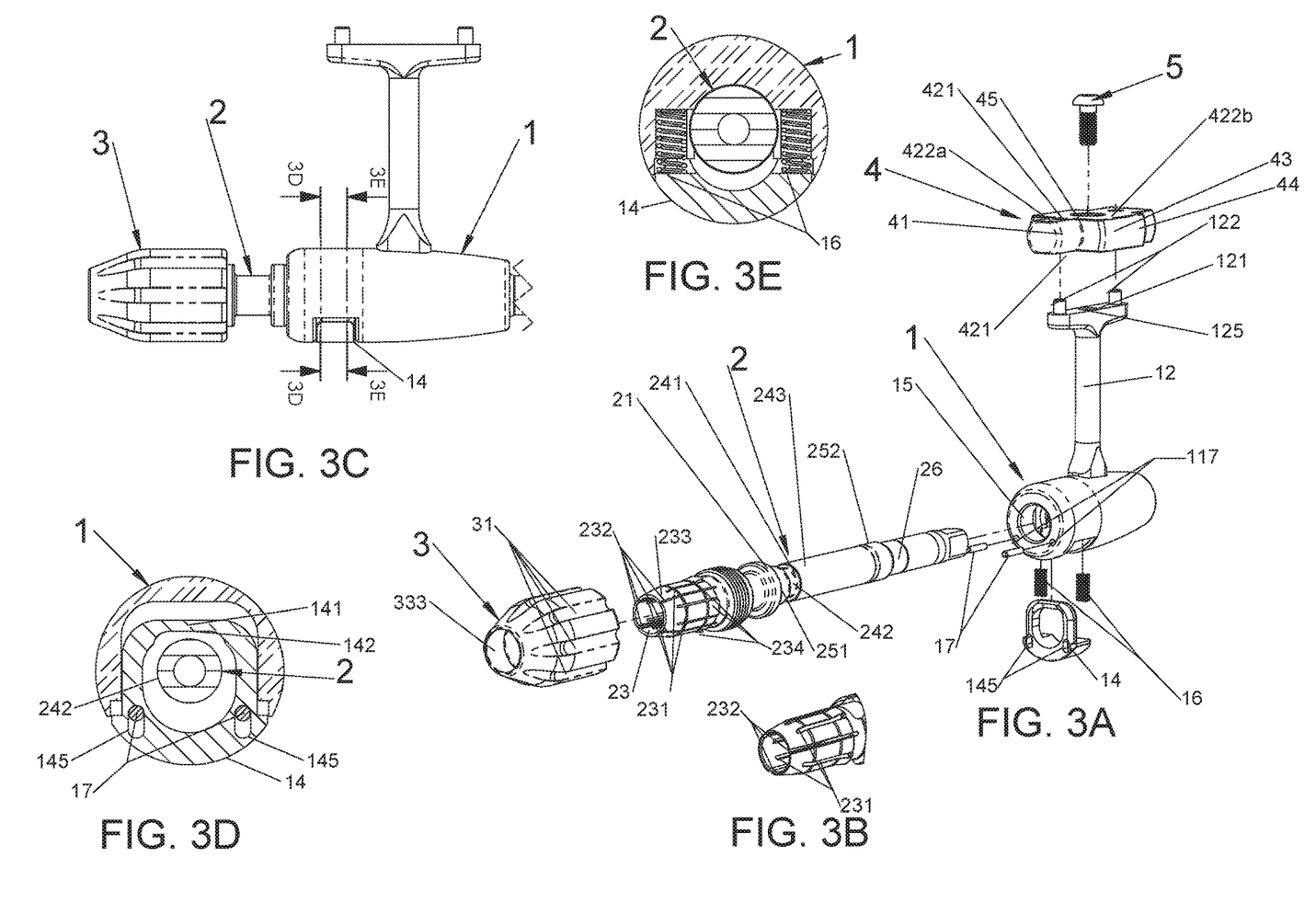
FIG. 3A is an exploded view of a universal instrument adapter, in accordance with an exemplary embodiment.
FIG. 3B is a detail view of an instrument connection portion of a universal instrument adapter, in accordance with an exemplary embodiment.
FIG. 3C is a side view of a universal instrument adapter, in accordance with an exemplary embodiment.
FIG. 3D is a detailed cross-section view of a portion of a locking button portion of a universal instrument adapter, in accordance with an exemplary embodiment.
FIG. 3E is a detailed cross-section view of a portion of a locking button portion of a universal instrument adapter, in accordance with an exemplary embodiment.

FIG. 3A is an exploded view of a universal instrument adapter, in accordance with an exemplary embodiment. In this example, the instrument nut (3) is shown distal of the drive shaft (2), and the tracking array holder (1) proximal the drive shaft (2). The instrument nut (3) can include distal conical interface (333) and grooves (31) around the outer circumference, which create a ribbed surface to enhance grip. Moving proximally, the instrument connection (23) portion of the drive shaft (2) is illustrated including slot openings (231, 232) in the cylindrical portion of the instrument connection (23) that forms a bore to receive an instrument. The instrument connection conical interfaces (233, 234) are also shown on outer surfaces of the cylindrical portion of the instrument connection (23). While not numbered in FIG. 3A, the threaded portion of the distal end of the drive shaft (2) is also shown, the threaded portion of the drive shaft (2) receives the instrument nut (3) when assembled.

The drive shaft (2) can also include positioning flange (21) that extends radially outward from a distal end of the intermediate cylinder (251). On a proximal side of the intermediate cylinder (251) is the circular locking groove (242) that includes locking groove face (241). Continuing proximally, the drive shaft (2) can include the shaft lock section (243) and intermediate cylinder (252). As discussed above, when the drive shaft (2) is inserted into the tracking array holder (1), the device holder inner bore (15) mates with the intermediate cylinders (251, 252).

Illustrated proximal to the drive shaft (2) is the tracking device holder (1). In this example, the tracking device holder (1) includes the device holder inner bore (15), which receives the drive shaft (2). Inferior to the opening of the device holder inner bore (15) are retention pin bores (117) to receive retention pins (17). In this example, the retention pins (17) can retain the locking button (14) through engagement with the retention pin grooves/slots (15) after the locking button (14) is inserted into the adapter body (11). The locking button (14) is inserted into the adapter body (11) with two lock button springs (16) to bias the locking button (14) into a locked position. The locking button (14) and lock button springs (16) are illustrated inferior to the tracking array holder (1), as they are assembly into a slot on an inferior portion of the tracking array holder (1).

The tracking array pedestal (6) is illustrated with a universal support (4) set to engage positioning pins (122), which extend superiorly from the interface surface (121). The universal support (4) can include tracker clamping surfaces (41, 43, 44), screw hole (45), superior and inferior surfaces (421), a distal locating bore (422a), and a proximal locating bore (422b). The positioning pins (122) engage with the distal locating bore (422a) and the proximal locating bore (422b), and the screw (5) secures the universal support (4) through the screw hole (45) and into threaded hole (125). In this example, the universal support (4) is positioned superior to the longitudinal axis by the extension rod (12).

FIG. 3B is a detail view of an instrument connection (23) portion of a universal instrument adapter, in accordance with an exemplary embodiment. In this example, the instrument connection (23) is shown with detail illustrating slot openings (231, 232). In this example, the slot openings (232) extend from and interrupt the outer rim of the instrument connection (23). The slot openings (232) create three semi-cylindrical tangs extending distally from the area of the drive socket of the instrument connection (23). In this example, the slot openings (231) extend only a portion of the longitudinal distance of the slot openings (232) to provide some additional flexibility for the three semi-cylindrical tangs.

FIG. 3C is a side view of a universal instrument adapter, in accordance with an exemplary embodiment. The side view provided in FIG. 3C illustrates the major components of the universal adapter including the tracking device holder (1), the drive shaft (2), and the instrument nut (3). Additionally, the side view is used to show where cross-sections of the locking button (14) shown in FIGS. 3D and 3E fit into the overall device.

FIG. 3D is a detailed cross-section view of a section of the locking button (14) portion of a universal instrument adapter, in accordance with an exemplary embodiment. In this example, the cross-section of the locking button (14) illustrates structures such as the tracking device holder (1), the drive shaft (2), axial lock surface (141), inner superior lock surface (142), retention pin slots (145), retention pins (17), and circular locking groove (242). The locking button (14) can linearly translate within the tracking device holder (1) and is retained by retention pins (17) captured within retention pin slots (145). When biased radially outward, the axial lock surface (141) and inner superior lock surface (142) engage with portions of the drive shaft (2) including the circular locking groove (242). Engagement of the axial lock surface (141) and the inner superior lock surface (142) with the circular locking groove (242) maintains the axial position of the tracking array holder (1) relative to the drive shaft (2). The circular locking groove (242) ensures that rotation around the longitudinal axis is maintained with the tracking array holder (1) locked into axial position along the drive shaft (2).

FIG. 3E is a detailed cross-section view of a portion of a locking button (14) portion of a universal instrument adapter, in accordance with an exemplary embodiment. The second cross-section of locking button (14) illustrates the biasing springs, lock button springs (16), engaging with the tracking device holder (1) on either side of the drive shaft (2).

Figures 4A, 4B, 4C:
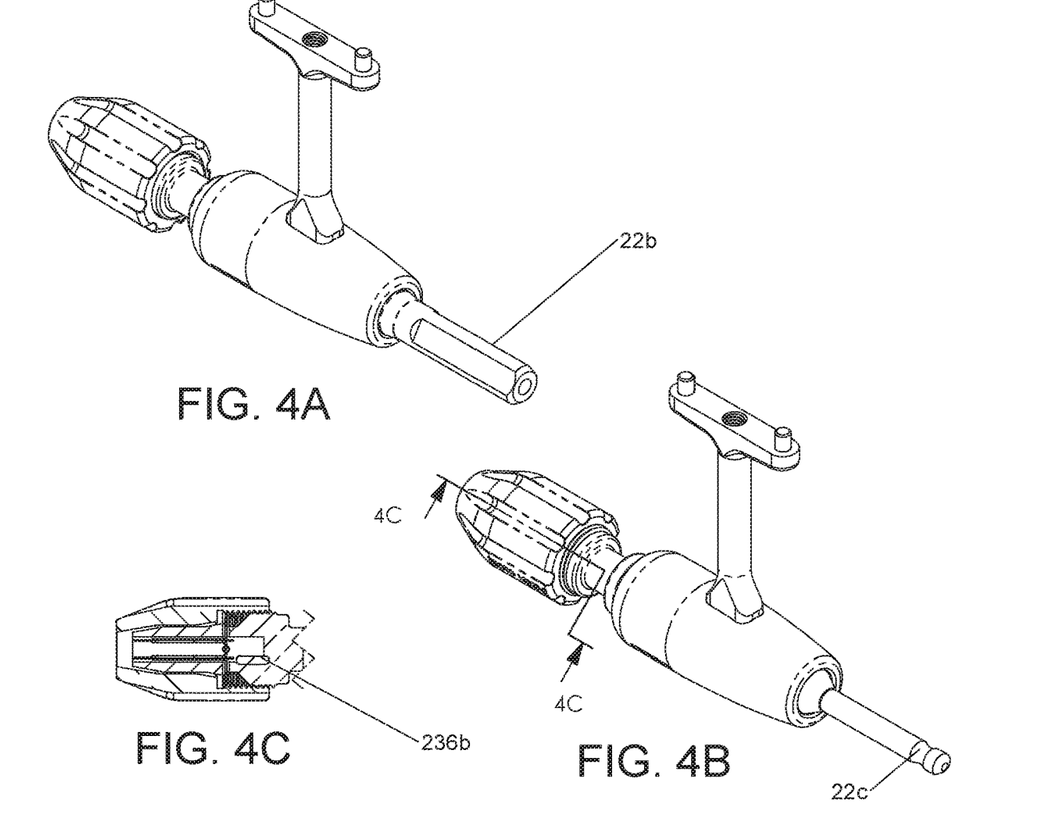
FIGS. 4A, 4B, 4D, and 4E are perspective views of universal adapters with various different handle connector types, in accordance with various exemplary embodiments.
FIG. 4C is a cross-section view of a portion of the instrument connection portion of a universal adapter, in accordance with an exemplary embodiment.
Figures 4D, 4E:
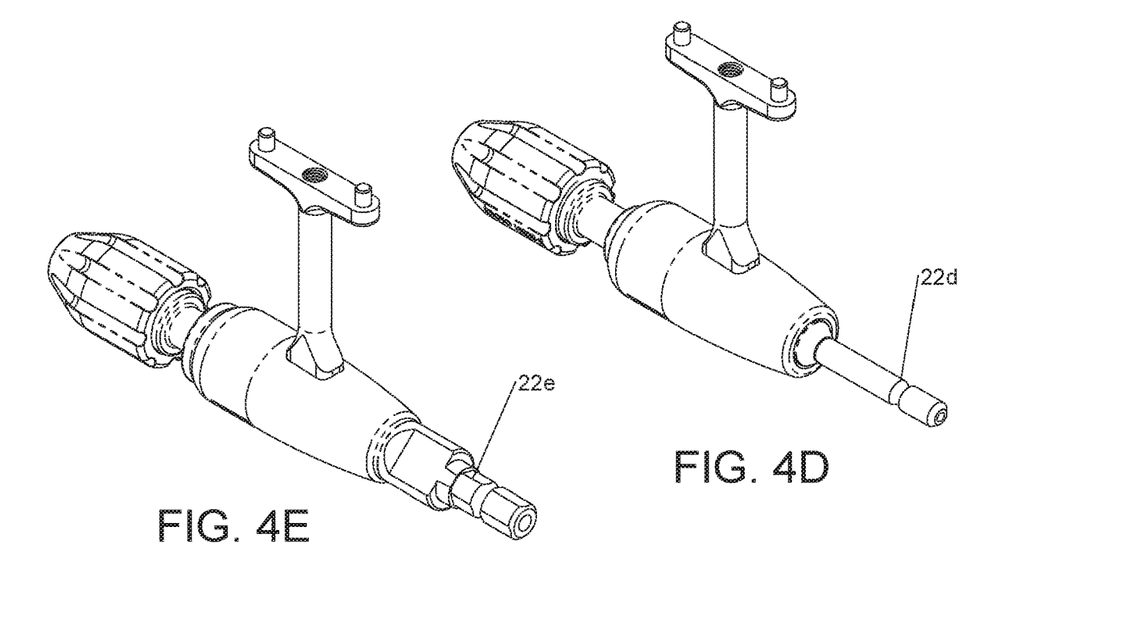

FIGS. 4A, 4B, 4D, and 4E are perspective views of universal adapters with various different handle connector types, in accordance with various exemplary embodiments. FIG. 4A illustrates a tri-flat handle connector (22b). FIG. 4B illustrates an "AO" quick connect handle connector (22c). FIG. 4D illustrates an "AO" large quick connect type of handle connector (22d). FIG. 4E illustrates a Hudson type of handle connector (22e), which is capable of delivering high torque. Any of the example handle connectors can also be coupled to an appropriate powered instrument with a compatible mating interface.

FIG. 4C is a cross-section view of a portion of the instrument connection (23) portion of a universal adapter, in accordance with an exemplary embodiment. In this example, an "AO" female quick connect drive connector (236b) is illustrated in cross-section.

Figure 5A:
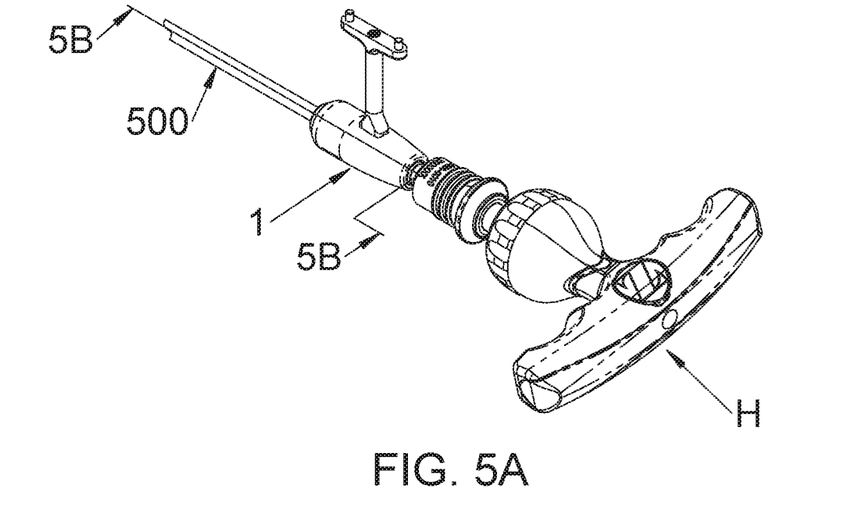
FIG. 5A is a perspective view of a navigation adapter for direct connection to an instrument, in accordance with an exemplary embodiment.

FIG. 5A is a perspective view of a navigation adapter for direct connection to an instrument, in accordance with an exemplary embodiment. In this example, the tracking array holder (1) is received directly onto an instrument (500) adapted to include the necessary aspects of the drive shaft (2) discussed above. In this example, the instrument (500) includes a handle (H) couplable to the proximal end.

Figure 5B:
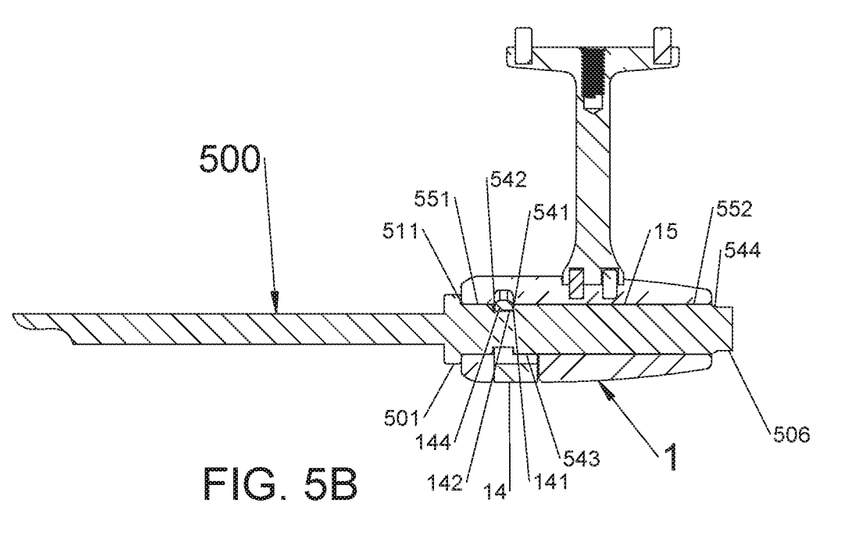
FIG. 5B is a cross-section view of a navigation adapter for direct connection to an instrument, in accordance with an exemplary embodiment.

FIG. 5B is a cross-section view of a navigation adapter for direct connection to an instrument, in accordance with an exemplary embodiment. The cross-section view illustrates details of the instrument (500) that enable use of the tracking array holder (1) directly on the instrument (500). In this example, the instrument (500) includes a positioning flange (501) that has a positioning flange face (511). Similar to positioning flange face (211) discussed above, the positioning flange face (511) abuts a surface on the tracking array holder (1) to maintain a fixed axial position along the longitudinal axis of the instrument (500). The instrument (500) also includes proximal and distal intermediate cylinders (551, 552), which interface with the device holder inner bore (15) to radially position the tracking array holder (1). The instrument (500) further includes a shaft lock section (543) that has a circular locking groove (542) and a locking groove face (541), with interact with the locking button (14). Finally, the instrument (500) includes instrument shaft bevel (544) that increases the diameter of the instrument from the handle shaft portion (506) to the proximal intermediate cylinder (552). The features of the instrument (500) discussed here operate and interact with the tracking array holder (1) in a manner similar to comparable structures discussed above in reference to the drive shaft (2).

The systems, devices and methods discussed in the present application can be useful in performing registration processes of fiducial markers with robotic surgical systems, such as by improving the accuracy of the registration process. In particular, the systems, devices and methods described herein facilitate more precise engagement between a pointer probe tip and a fiducial marker and better recognition of proper engagement between a pointer probe tip and the fiducial marker by an operator or surgeon. Such benefits can reduce error in the registration process, which can correlate to reduced error in performing a medical procedure on a patient.

Various Notes & Examples

Example 1 includes a universal adapter for coupling a navigation tracking array to an instrument. The universal adapter can include a drive shaft and a tracking device holder. In this example, the drive shaft can include a proximal handle interface, a distal instrument connection, and an intermediate section extending proximally from a distal positioning flange and including an enlarged diameter and a circular locking groove. The tracking device holder can be configured to secure a navigation tracking array to the drive shaft. The tracking device holder can include an elongated body having an inner bore extending along a longitudinal length of the elongated body and adapted to receive the intermediate section of the drive shaft. The tracking device holder can also include a locking button engagable with the circular locking groove to retain the tracking device holder in a fixed axial position along a longitudinal axis of the drive shaft while allowing for rotation of the tracking device holder about the longitudinal axis.

In example 2, the subject matter of example 1 can optionally include the locking button having a biasing mechanism to maintain contact with the circular locking groove and enable selective disengagement.

In example 3, the subject matter of example 2 can optionally include the biasing mechanism having a plurality of springs.

In example 4, the subject matter of any one of examples 1 to 3 can optionally include the locking button having an offset central bore including an inner superior lock surface biased into the circular locking groove when the locking button is engaged with the circular locking groove.

In example 5, the subject matter of any one of examples 1 to 4 can optionally include the distal instrument connection having an instrument nut comprising an internally threaded bore to engage an externally threaded portion of the drive shaft.

In example 6, the subject matter of example 5 can optionally include the instrument nut having an internal conical surface distal the internally threaded bore.

In example 7, the subject matter of example 6 can optionally include the distal instrument connection having a compressible section including a distal conical interface and a plurality of slot openings.

In example 8, the subject matter of example 7 can optionally include threading the instrument nut onto the distal instrument connection secures an instrument to the drive shaft via compression of the compressible section through interaction of the distal conical interface and the internal conical surface of the instrument nut.

In example 9, the subject matter of example 7 can optionally include at least a portion of the plurality of slot openings extending to a distal most end of the drive shaft.

Example 10 can include a universal adapter apparatus. The apparatus can include a drive shaft and a tracking device holder. In this example, the drive shaft can include a proximal handle interface, a distal instrument connection, and an intermediate section extending proximally from a distal positioning flange and including a circular locking groove, distal instrument connection adapted to removably and securely couple a proximal end of a plurality of instruments to the drive shaft. The tracking device holder can include an elongated body and a locking button. The elongated body can include an inner bore extending along a longitudinal length of the elongated body and adapted to receive the intermediate section of the drive shaft. The locking button can be engagable with the circular locking groove to retain the tracking device holder in a fixed axial position along a longitudinal axis of the drive shaft while allowing for rotation of the tracking device holder about the longitudinal axis.

In example 11, the subject matter of example 10 can optionally include the tracking device holder having a universal support coupled to the tracking array pedestal via the plurality of locating pins.

In example 12, the subject matter of example 11 can optionally include the universal support having a plurality of clamping interfaces.

In example 13, the subject matter of example 12 can optionally include each clamping interface of the plurality of clamping interfaces includes opposing radiused sidewalls with a different cross-sectional diameter.

In example 14, the subject matter of any one of examples 10 to 13 can optionally include the tracking array pedestal receiving a tracking array directly on the plurality of locating pins.

In example 15, the subject matter of example 14 can optionally include the integrated tracking array having a plurality of tracking markers arranged in a fixed spatial relationship.

In example 16, the subject matter of any one of examples 14 or 15 can optionally include the tracking array is secured to the tracking array pedestal via a fastener.

In example 17, the subject matter of any one of examples 10 to 15 can optionally include each locating pin of the plurality of locating pins is a unique shape to ensure a unique mounting position for a navigation tracking array in reference to the elongated body.

In example 18, the subject matter of any one of examples 10 to 17 can optionally include the distal instrument connection having an instrument bore adapted to receive the proximal end of the plurality of instruments.

In example 19, the subject matter of example 18 can optionally include the instrument bore having a plurality of slot openings distributed around the circumference, where each slot opening of the plurality of slot openings defines a longitudinal opening through a cylindrical structure forming the instrument bore.

In example 20, the subject matter of example 19 can optionally include at least a portion of the plurality of slot openings creating breaks in a distal most rim of the cylindrical structure forming the instrument bore.

In example 21, the subject matter of any one of examples 19 or 20 can optionally include the distal instrument connection having an instrument nut threadably engagable with the drive shaft to secure the proximal end of the plurality of instruments.

In example 22, the subject matter of any one of examples 10 to 21 can optionally include the proximal handle interface being a ¼" (¼ inch or quarter-inch) square drive quick connect.

Each of these non-limiting examples can stand on its own, or can be combined in various permutations or combinations with one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventor also contemplates examples in which only those elements shown or described are provided. Moreover, the present inventor also contemplates examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. A universal adapter for coupling a navigation tracking array to an instrument, the universal adapter comprising:
    a drive shaft including a proximal handle interface, a distal instrument connection comprising an instrument bore adapted to receive a proximal end of the instrument, and an intermediate section extending proximally from a distal positioning flange and including an enlarged diameter and a circular locking groove; and
    a tracking device holder configured to secure the navigation tracking array to the drive shaft, the tracking device holder comprising:
        an elongated body including an inner bore extending along a longitudinal length of the elongated body and adapted to receive the intermediate section of the drive shaft; and
        a locking button inserted into the elongated body and engageable with the circular locking groove to retain the tracking device holder in a fixed axial position along a longitudinal axis of the drive shaft while allowing for rotation of the tracking device holder about the longitudinal axis, wherein the locking button includes an offset central bore, and wherein the intermediate section of the drive shaft is insertable into the inner bore of the elongated body and into the offset central bore of the locking button.

2. The universal adapter of claim 1, wherein the offset central bore includes an inner superior lock surface biased into the circular locking groove when the locking button is engaged with the circular locking groove, wherein the inner superior lock surface is positionally opposite of an engagement surface of the locking button that extends from the elongated body relative to the circular locking groove.

3. The universal adapter of claim 1, wherein the locking button includes a biasing mechanism to maintain contact with the circular locking groove on at least two sides of the circular locking groove and enable selective disengagement.

4. The universal adapter of claim 3, wherein the biasing mechanism includes a plurality of springs.

5. The universal adapter of claim 1, wherein the drive shaft comprises a single-piece drive shaft, and wherein the distal instrument connection includes an instrument nut comprising an internally threaded bore to engage an externally threaded portion at a distal end of the single-piece drive shaft about the instrument bore.

6. The universal adapter of claim 5, wherein the instrument nut includes an internal conical surface distal the internally threaded bore.

7. The universal adapter of claim 6, wherein the distal instrument connection includes a compressible section including a distal conical interface and a plurality of slot openings.

8. The universal adapter of claim 7, wherein the instrument nut is configured to thread onto the externally threaded portion at the distal end of the single-piece draft shaft to secure the instrument to the single-piece drive shaft via compression of the compressible section through interaction of the distal conical interface and the internal conical surface of the instrument nut.

9. The universal adapter of claim 7, wherein at least a portion of the plurality of slot openings extend to the distal end of the single-piece drive shaft.

10. A universal adapter apparatus comprising:
    a drive shaft including a proximal handle interface, a distal instrument connection, and an intermediate section extending proximally from a distal positioning flange and including a circular locking groove, the distal instrument connection comprising an instrument bore adapted to receive and removably and securely couple a proximal end of a plurality of instruments to the drive shaft; and
    a tracking device holder adapted to maintain at least one navigation tracking array in a fixed axial position relative to a longitudinal axis of the drive shaft, the tracking device holder comprising:
- an elongated body including an inner bore extending along a longitudinal length of the elongated body, the elongated body adapted to receive the intermediate section of the drive shaft within the inner bore and within an offset central bore of a locking button inserted into the elongated body, an inner superior lock surface of the offset central bore being positionally substantially opposite of an engagement surface of the locking button extending from the elongated body relative to the circular locking groove, the elongated body further adapted to engage a portion of the intermediate section of the drive shaft and abut the distal positioning flange while remaining rotatable around the longitudinal axis of the drive shaft; and
- a tracking array pedestal coupled to the elongated body via an extension rod and including a plurality of locating pins, the tracking array pedestal adapted to couple the at least one navigation tracking array with a plurality of clamping mechanisms to the tracking device holder.

11. The universal adapter apparatus of claim 10, wherein each locating pin of the plurality of locating pins is a unique shape to ensure a unique mounting position for the at least one navigation tracking array in reference to the elongated body.

12. The universal adapter apparatus of claim 10, wherein the proximal handle interface is a ¼-inch square drive quick connect.

13. The universal adapter apparatus of claim 10, wherein the tracking device holder includes a universal support coupled to the tracking array pedestal via the plurality of locating pins.

14. The universal adapter apparatus of claim 13, wherein the universal support includes a plurality of clamping interfaces.

15. The universal adapter apparatus of claim 14, wherein each clamping interface of the plurality of clamping interfaces includes opposing radiused sidewalls with a different cross-sectional diameter.

16. The universal adapter apparatus of claim 10, wherein the tracking array pedestal receives the at least one navigation tracking array directly on the plurality of locating pins.

17. The universal adapter apparatus of claim 16, wherein the at least one navigation tracking array includes a plurality of tracking markers arranged in a fixed spatial relationship.

18. The universal adapter apparatus of claim 16, wherein the at least one navigation tracking array is secured to the tracking array pedestal via a fastener.

19. The universal adapter apparatus of claim 10, wherein the instrument bore includes a plurality of slot openings distributed around the circumference, wherein each slot opening of the plurality of slot openings defines a longitudinal opening through a cylindrical structure forming the instrument bore.

20. The universal adapter apparatus of claim 19, wherein at least a portion of the plurality of slot openings create breaks in a distal most rim of the cylindrical structure fanning the instrument bore.

21. The universal adapter apparatus of claim 19, wherein the drive shaft comprises a single-piece drive shaft, and wherein the distal instrument connection includes an instrument nut threadably engagable with the single-piece drive shaft about the instrument bore to secure the proximal end of the plurality of instruments.

22. A universal adapter for coupling a navigation tracking array to an instrument, the universal adapter comprising:
- a single-piece drive shaft including a proximal handle interface, an instrument nut comprising an internally threaded bore to engage an externally threaded portion at a distal end of the single-piece drive shaft, and an intermediate section extending proximally from a distal positioning flange and including an enlarged diameter and a circular locking groove; and
- a tracking device holder configured to secure the navigation tracking array to the single-piece drive shaft, the tracking device holder comprising:
  - an elongated body including an inner bore extending along a longitudinal length of the elongated body and adapted to receive the intermediate section of the single-piece drive shaft; and
  - a single locking button including a first section with an offset central bore operable to receive the single-piece drive shaft and a second section with a groove, the single locking button being engageable with the circular locking groove to retain the tracking device holder in a fixed axial position along a longitudinal axis of the single-piece drive shaft while allowing for rotation of the tracking device holder about the longitudinal axis, wherein an inner superior lock surface of the first section of the offset central bore of the single locking button is biasable into the circular locking groove via a biasing mechanism when the locking button is engaged with the circular locking groove, and wherein the biasing mechanism is positioned between the elongated body and the second section on at least two sides of the circular locking groove.

* * * * *